United States Patent [19]
Levine et al.

[11] Patent Number: 5,086,784
[45] Date of Patent: Feb. 11, 1992

[54] CENTRIFUGED MATERIAL LAYER MEASUREMENTS TAKEN IN AN EVACUATED TUBE

[76] Inventors: Robert A. Levine, 31 Pilgrim La., Guilford, Conn. 06437; Stephen C. Wardlaw, 191 North Cove Rd., Old Saybrook, Conn. 06475

[21] Appl. No.: 579,274

[22] Filed: Sep. 5, 1990

Related U.S. Application Data

[63] Continuation of Ser. No. 356,077, May 24, 1989, abandoned.

[51] Int. Cl.⁵ .................................................. A61B 5/14
[52] U.S. Cl. .................................. 128/771; 128/760; 210/789
[58] Field of Search ................. 128/760–764, 128/771; 210/359, 513, 516, 782, 789

[56] References Cited

U.S. PATENT DOCUMENTS

| | | | |
|---|---|---|---|
| 3,931,018 | 1/1976 | North, Jr. | 210/359 |
| 4,012,325 | 3/1977 | Columbus | 128/764 X |
| 4,492,634 | 1/1985 | Villa-Real | 210/359 X |
| 4,770,779 | 9/1988 | Ichikawa et al. | 210/516 |
| 4,774,965 | 10/1988 | Rodriguez et al. | 128/771 |
| 4,853,137 | 8/1989 | Ersson | 210/516 |
| 4,867,887 | 9/1989 | Smith | 210/516 X |

*Primary Examiner*—Robert A. Hafer
*Assistant Examiner*—Kerry Owens
*Attorney, Agent, or Firm*—William W. Jones

[57] ABSTRACT

Centrifuged material layer measurements are made in an evacuated glass or clear plastic tube which contains a float. When possibly contaminated materials, such as blood, are being tested the use of the evacuated tube allows the measurements to be made without the technician being exposed to the blood. The tubes are large enough to hold approximately one ml of blood, and are filled with an inert gas at low pressure. Dimensional tolerances relative to those of a capillary tube are relaxed for the tube and float due to the larger sample capacity. The cell bands are stabilized by a layer of a flowable material which settles onto the plasma layer during centrifugation and forms a pellicle thereon.

9 Claims, 1 Drawing Sheet

CENTRIFUGED MATERIAL LAYER MEASUREMENTS TAKEN IN AN EVACUATED TUBE

This application is a continuation of application Ser. No. 07/356,077, filed May 24, 1989, aband.

This invention relates to paraphenalia for determining material layer volume values in a centrifuged sample of a material such as blood. The tests are performed in an evacuated tube containing a float which expands the layers being measured.

A technique has been developed to measure constituent layers in a complex material mixture by centrifuging a sample of the material mixture in a capillary or other tube which contains a float. The float is preferably cylindrical and of a specific gravity which causes it to settle into the centrifuged mixture to a degree which creates a free volume annulus in the tube into which the layer, or layers to be measured will settle. The layers to be measured are thus physically elongated, and can be more easily and accurately measured. This technique is described in U.S. Pat. Nos. 4,027,660, issued June 7, 1977; 4,082,085 issued Apr. 4, 1978; 4,156,570 issued May 29, 1979; and others.

When the material being tested is a possibly contaminated material such as blood, it is desirable to make provisions for protecting the technician against exposure to the blood. When the aforesaid prior art techniques are performed with capillary tubes, the person performing the test is exposed to the blood since the capillary tubes are open-ended. Thus, despite taking normal precautions in handling of the samples, the chance of being contaminated by a blood sample exists.

This invention is directed to paraphenalia for use in the collecting and testing of a possibly contaminated material such as blood, wherein the person doing the testing is never exposed to the blood. No transfer of blood from a collection vessel to the measurement tube is needed. Thus, the possibility of becoming infected by a contaminated blood sample is eliminated. When the tube and float of this invention are used, the blood sample is collected and tested in a sealed tube, and the blood never leaves the confines of the tube after it is collected. An additional advantage of the invention resides in the fact that it entails the use of a unitary sealed tube which contains all of the required components for use in performing the cell counts, and those components are disposed in a stable, inert environment. The tube used in this invention is preferably a glass tube with an integral closed end. It will be the same length as a capillary tube but will have a larger diameter so as to be able to contain about 0.9 ml of blood. A cylindrical float is disposed inside of the tube, which float has an accurately controlled outside diameter so as to operate to physically expand the white cell and platelet layers in the blood sample after centrifugation thereof. The float is made from a plastic material having a specific gravity that causes it to float in the packed red cells after centrifugation of the blood sample in the tube. The required reagents such as a stain and a red cell densifier, preferably potassium oxalate, are disposed in the tube, preferably in liquid form. An elastomeric stopper closes the open end of the tube, and the interior of the tube is filled with an inert gas at low pressure. The low pressure in the tube is used to draw the blood sample into the tube, either directly from a vein, or directly through a double pointed needle from a primary blood collection device, such as that sold by Becton Dickinson and Company under the trademark "Vacutainer".

When the sample is taken from a patient in a primary blood collection tube, the collection tube will be provided with a needle which is used to pierce the elastomeric stopper in the tube of this invention, whereupon the blood will flow from the collection tube, through the needle, into the testing tube. In order to preserve cell band formation in the tube when the tube and blood are centrifuged, a thixotropic gel will be disposed in the top of the tube. During centrifugation, the gel will flow in the tube and settle on top of the plasma layer to form a viscous pellicle on the plasma. Obviously, the gel must have a specific gravity which is less than that of the plasma. An example of a suitable gel is silicone gel.

When the larger bore diameter tubes and larger floats are used per this invention, there occurs a relaxation in the diameter dimensional tolerances, between the tube bore ID and the float OD. It is desirable to achieve a ten fold expansion of the white cell and platelet layers when performing the cell count measurements with the tube-float combination of the aforesaid prior art. When using the enlarged tubes and floats of this invention, the ten fold expansion can be obtained from an annular free space of about 125 microns between the tube bore and float. This compares with a free space of about 43 microns with the prior art capillary tubes and floats. The resultant larger free volume space provides a relaxation of dimensional tolerances required for an accuracy of 5% by about three fold.

Another benefit deriving from the use of the larger tube and float paraphenalia is the improvement in the hydrodynamics of cell distribution in the white cell and platelet area. Because of the larger annulus volume, and larger blood sample, more cells will be present in the expanded layers than with the prior art. This will result in a freer percolation of plasma through the white cell and platelet layers during centrifugation whereby better defined and more compact cell band formation will result.

It is therefore an object of this invention to provide an improved blood sampling paraphenalia which allows for the blood cell counts to be made without exposing the technician to contamination from the blood sample.

It is a further object of this invention to provide blood sampling paraphenalia of the character described wherein dimensional tolerances are relaxed while providing the necessary cell layer expansion.

It is an additional object of this invention to provide blood sampling paraphenalia of the character described wherein larger blood samples are tested.

It is still another object of this invention to provide blood sampling paraphenalia of the character described wherein the formation of cell bands after centrifugation, is stabilized and preserved.

It is yet an additional object of this invention to provide blood sampling paraphenalia of the character described wherein improved percolation of blood cells during centrifugation is achieved.

These and other objects and advantages of the invention will become more readily apparent from the following description of a preferred embodiment thereof when considered in conjunction with the accompanying drawings, in which.

Figure 1:
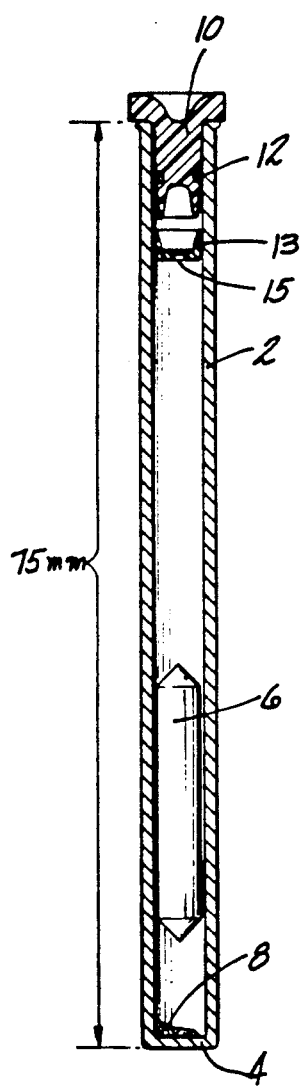
FIG. 1 is an axial sectional view of a preferred embodiment of a tube and float assembly formed in accordance with this invention.

Referring now to the drawings, there is shown in FIG. 1 a preferred embodiment of the blood sampling paraphenalia formed in accordance with this invention. The blood sampling paraphenalia includes a transparent tube 2 formed preferably of glass, and having an integrally closed end 4. A plastic float member 6 is disposed in the tube 2, as are the stain and red cell densifier reagents 8. An elastomeric plug 10 closes the open end of the tube 2, and a supply of a thixotropic gel 12 is disposed inside of the tube 2 around the plug 10. In place of the gel 12, a plastic disk 13 can be used to cap the centrifuged blood sample in the tube 2. The disk 13 has an opening 15 in it which is about the diameter of a capillary tube bore. The tube is preferably about 75 mm long, the same length as a capillary tube, and has a bore diameter of about 40 mm. Its capacity for blood is about 0.9 ml. The float will be about 2 cm in length and about 37.9 mm in diameter.

Figure 2:
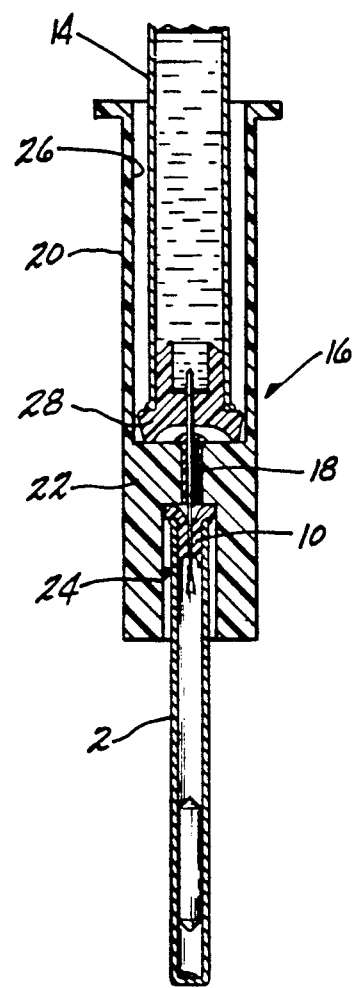
FIG. 2 is an axial sectional view similiar to FIG. 1 but showing how the assembly can be used to draw a blood sample from a primary blood collecting tube.

FIG. 2 shows how the tube 2 can be filled with blood from a primary blood collecting tube 14 by means of a transferring device 16 having a double piercing needle or cannula 18. The transfer device 16 includes an outer shroud 20 with a needle-carrying plug 22 telescoped thereinto. The needle 18 extends into a first well 24 in the plug 22 sized to receive the stoppered end of the blood sampling tube 2. The shroud 20 forms a second well 26 which is sized to receive the stoppered end of the primary blood collecting tube 14. The transfer needle 18 pierces the plug 28 in the tube 14 and also pierces the plug 10 in the sampling tube 2. The low pressure in the tube 2 causes blood to be drawn from the tube 14 through the needle 18 into the tube 2, the flow of blood continuing until the tube 2 is substantially filled. Once filled, the tube 2 is withdrawn from the well 24 and centrifuged. While transferring blood to the testing tube 2 from a collection tube 14 is one way to fill the tube 2, it is readily apparent that the sample could be taken directly from a patient using a needle and the evacuated tube 2.

Figure 3:
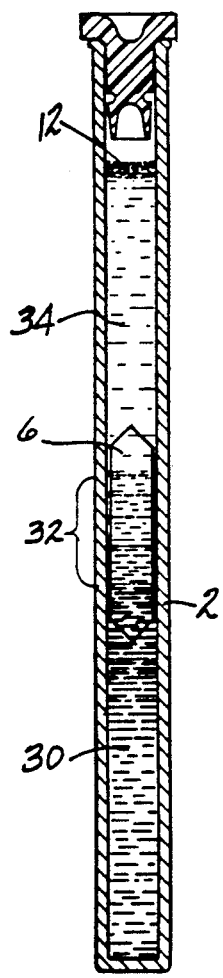
FIG. 3 is a view similar to FIGS. 1 and 2 but showing the assembly of FIG. 1 after the blood sample has been drawn and centrifuged.

When the blood enters the tube 2, the reagents 8 will mix with the blood, and the tube 2 will be ready to centrifuge. The tubes 2 are oriented in the centrifuge with the closed end 4 out, so that the red cells will settle in the closed end of the tube 2 and the plasma will be adjacent to the stoppered end of the tube 2 after centrifugation. FIG. 3 shows the condition of the tube 2 and blood after the centrifugation has been completed. The red cells 30 collect in the closed end of the tube 2 and the float 6 floats in, and projects above the top of the red cell layer. The white cells and platelet layers which make up the buffy coat 32 settle into the area between the float 10 and the bore wall of the tube, and the plasma 34 is disposed above the buffy coat and float 10. The thixotropic gel covers and floats on the plasma layer 34 thereby holding the centrifuged blood constituent layers in place when the tube 2 is handled after the centrifugation step during measurement of the cell band thicknesses. The tube 2 can thus be placed in a reader instrument of the type generally disclosed in the aforesaid prior art without disrupting the centrifuged cell bands, so that the axial lengths of the white cell and platelet bands can be measured and converted to cell count information by the reader instrument microprocessor.

It will be readily appreciated that the tubes of this invention can be used to draw blood samples from patients or from blood collecting tubes, and the blood cell measurements can then be made directly in the stoppered, closed tubes without exposing anyone to the possibility of contact with contaminated blood. Thus the blood testing procedure can even be used with patients who are known to have contaminated blood greatly reducing the danger to the person doing the testing. The dimensional tolerances observed in producing the tubes and floats are relaxed, and the test assemblies have a longer shelf life since the interior of the evacuated tubes is filled with an inert gas. Cell layer band formation is preserved during handling of the tube after centrifugation due to the pellicle formed on top of the plasma by the thixotropic material during centrifugation.

Since many changes and variations of the disclosed embodiment of the invention may be made without departing from the inventive concept, it is not intended to limit the invention otherwise than as required by the appended claims.

What is claimed is:

1. A blood sampling assembly for performing tests on a centrifuged sample of blood contained in the assembly without exposing one performing the test to the blood being sampled, said assembly comprising: a transparent tube for holding the sample of blood, said tube having an integral end wall closing one end thereof; an elongated float member disposed in said tube, said float member being operable to settle into the red blood cell layer of the centrifuged blood sample and being sized to extend through the blood sample buffy coat and into the plasma layer and to provide an annular free space of about 125 microns between the tube bore and float and to physically expand the white cell and platelet layers in the buffy coat by about ten fold sufficiently to obtain white cell and platelet layer counts; testing reagents disposed in said tube for reacting with the blood cells to enhance results of the tests; an elastomeric stopper sealing the end of said tube opposite said integral end wall; and the interior of said tube having a subatmospheric pressure whereby the blood will be automatically drawn into said tube when said stopper is pierced by a blood Gampling needle.

2. The assembly of claim 1 wherein said tube contains an inert gas prior to use of the assembly to draw a blood sample.

3. The assembly of claim 1 further comprising means in said tube for forming a cap on top of the plasma layer of the blood sample during centrifugation to positionally stabilize the centrifuged blood constituent layers during handling of the assembly after centrifugation.

4. The assembly of claim 3 wherein said means for forming a cap is a flowable thixotropic material deposited in said tube.

5. The assembly of claim 3 wherein said means for forming a cap is a plastic disk oprerable to settle onto the plasma layer in the centrifuged blood sample.

6. The assembly of claim 4 wherein said tube is approximately equal in length to a conventional capillary tube and sized to contain approximately 0.9 ml of blood.

7. A blood sampling assembly for performing tests on a centrifuged sample of blood contained in the assembly, said assembly comprising: a transparent tube for holding the sample of blood, said tube being sealed at one end by an elastomeric stopper; an elongated float in said tube for physically elongating blood constituent layers in the centrifuged sample of blood; movable means in said tube for forming a blood constituent layer-stabilizing cap on top of the plasma layer of the centrifuged blood sample; and the interior of the tube having a pressure lowered to the extent needed to automatically draw blood into the tube when the stopper is pierced by a blood sampling needle.

8. The assembly of claim 7 wherein said movable means is a thixotropic substance deposited in said tube prior to centrifugation.

9. The assembly of claim 7 wherein said movable means is a disk operable to settle onto the plasma layer in the centrifuged blood sample.

* * * * *